United States Patent
Saunders et al.

(10) Patent No.: US 11,662,278 B2
(45) Date of Patent: *May 30, 2023

(54) SYSTEM AND METHOD FOR DETECTING AIRBORNE PATHOGENS

(71) Applicant: Kontrol Energy Corp., Vaughan (CA)

(72) Inventors: Gary Saunders, London (CA); Paul Ghezzi, King City (CA)

(73) Assignee: Kontrol Energy Corp., Vaughan (CA)

( * ) Notice: Subject to any disclaimer, the term of this patent is extended or adjusted under 35 U.S.C. 154(b) by 321 days.

This patent is subject to a terminal disclaimer.

(21) Appl. No.: 17/105,793

(22) Filed: Nov. 27, 2020

(65) Prior Publication Data

US 2022/0170827 A1    Jun. 2, 2022

(51) Int. Cl.
| | |
|---|---|
| *G01N 1/22* | (2006.01) |
| *G01N 21/77* | (2006.01) |
| *G01F 23/263* | (2022.01) |
| G01N 1/24 | (2006.01) |
| G01N 15/06 | (2006.01) |

(52) U.S. Cl.
CPC ......... *G01N 1/2202* (2013.01); *G01F 23/263* (2013.01); *G01N 1/2205* (2013.01); *G01N 1/2273* (2013.01); *G01N 21/77* (2013.01); G01N 2001/2282 (2013.01); G01N 2001/245 (2013.01); G01N 2015/0693 (2013.01)

(58) Field of Classification Search
CPC .. G01N 1/2202; G01N 1/2205; G01N 1/2273; G01N 21/77; G01N 2001/2282; G01N 2001/245; G01N 1/24; G01N 2015/0065; G01N 2015/0681; G01N 2015/0687; G01N 2015/0693; G01N 15/06; G01N 33/54366; G01F 23/263; G01F 23/261
See application file for complete search history.

(56) References Cited

U.S. PATENT DOCUMENTS

| | | | | |
|---|---|---|---|---|
| 6,054,324 A | * | 4/2000 | Sullivan | G01N 1/34 |
| | | | | 435/31 |
| 7,605,910 B2 | * | 10/2009 | Ahn | G01N 15/065 |
| | | | | 356/37 |
| 2019/0154550 A1 | * | 5/2019 | Wu | G01N 1/22 |

FOREIGN PATENT DOCUMENTS

CN          106092846 A    * 11/2016

OTHER PUBLICATIONS

Translation of CN106092846A, Zhang, Pei-hua, Nov. 9, 2016 (Year: 2016).*

* cited by examiner

*Primary Examiner* — Samuel P Siefke
*Assistant Examiner* — Henry H Nguyen
(74) *Attorney, Agent, or Firm* — Rowand LLP (57) ABSTRACT

An air sampling system is disclosed. The air sampling system includes: an air inflow channel having an air inlet portion at a top end, the air inflow channel being oriented substantially vertically; a fan configured to cause air in a sampling environment to flow into the air inflow channel via the inlet portion; a cooling unit for cooling air in the air inflow channel, the cooling unit disposed downstream of the inlet portion; a collection chamber for collecting liquid water condensed from air in the air inflow channel, the collection chamber being fluidly connected to the air inflow channel; and a sensing unit for determining a volume of liquid in the collection chamber, wherein the cooling unit is controlled in response to signals generated by the sensing unit.

18 Claims, 8 Drawing Sheets

FIG. 6A
SECTION B-B

Fig. 7

SYSTEM AND METHOD FOR DETECTING AIRBORNE PATHOGENS

TECHNICAL FIELD

The present application relates to air quality monitoring and, more particularly, to systems and methods for detecting presence of airborne pathogens in an indoor environment.

BACKGROUND

Conventional air monitoring systems measure the particulate matter content of air in an indoor environment. Such systems generally do not provide specific information identifying the types of particles that are present in the air. In crowded indoor environments, such as schools, hospitals, airports, malls, etc., it is desirable to be able to detect, in real-time, the presence of harmful agents (e.g. pathogens) in the air, in order to prevent and/or contain outbreaks.

BRIEF DESCRIPTION OF DRAWINGS

Reference will now be made, by way of example, to the accompanying drawings which show example embodiments of the present application and in which.

Like reference numerals are used in the drawings to denote like elements and features.

DETAILED DESCRIPTION OF EXAMPLE EMBODIMENTS

In one aspect, the present disclosure describes an air sampling system. The air sampling system includes: an air inflow channel having an air inlet portion at a top end, the air inflow channel being oriented substantially vertically; a fan configured to cause air in a sampling environment to flow into the air inflow channel via the inlet portion; a cooling unit for cooling air in the air inflow channel, the cooling unit disposed downstream of the inlet portion; a collection chamber for collecting liquid water condensed from air in the air inflow channel, the collection chamber being fluidly connected to the air inflow channel; a sensing unit for determining a volume of liquid in the collection chamber; and a controller configured to control the cooling unit based on signals generated by the sensing unit.

In some implementations, the sensing unit may be a level sensor associated with the collection chamber.

In some implementations, the level sensor may be a capacitive sensor.

In some implementations, the controller may be configured to control the cooling unit based on determining, from signals generated by the level sensor, whether a liquid level in the collection chamber deviates from a defined level.

In some implementations, the air sampling system may further include an air outflow channel that is fluidly connected to the collection chamber, the air outflow channel being oriented substantially vertically and the cooling unit may be further configured to cool air in the air outflow channel.

In some implementations, the cooling unit may include one or more cooling coils disposed downstream of the inlet portion, the one or more cooling coils being supported in thermal contact with at least a portion of the air inflow channel.

In some implementations, the cooling unit may include one or more cold plates disposed downstream of the inlet portion, the one or more cold plates being supported in thermal contact with at least a portion of the air inflow channel.

In some implementations, the one or more cold plates may be made of aluminum.

In some implementations, the air sampling system may further include a particulate monitor device for monitoring particulate matter content of air flowing into the air inflow channel.

In some implementations, the air sampling system may further include an air pump for drawing air out of the collection chamber via an air outflow channel.

In some implementations, the air pump may be a high-volume air sampling pump.

In some implementations, the sensing unit may be a temperature sensor for measuring a temperature of the air in the air inflow channel and the controller may be configured to control the cooling unit based on measurements obtained from the temperature sensor.

In some implementations, the collection chamber may include an active target substrate having a surface that is coated with bioreceptors and the air sampling system may further include an optical detection unit that is configured to illuminate the active target substrate with a light source.

In some implementations, the bioreceptors may be antibodies.

In some implementations, the air sampling system may further include: a liquid inflow channel having a liquid inflow port, the liquid inflow channel being fluidly connected to the collection chamber; a liquid outflow channel that is fluidly connected to the collection chamber; and a liquid pump for causing liquid to flow into and out of the collection chamber.

In some implementations, the sensing unit may be a flow sensor associated with at least one of the liquid inflow channel or the liquid outflow channel for measuring a rate of flow of liquid out of the collection chamber and the controller may be configured to control the cooling unit based on measurements obtained from the flow sensor.

In some implementations, the air sampling system may further include a hygroscopic filter that removes liquid from air that is expelled out of the collection chamber.

In some implementations, the collection chamber may be removably coupled to the air inflow channel.

In some implementations, the air sampling system may further include a plurality of glass beads disposed inside the collection chamber, the surfaces of the plurality of glass beads being exposed to liquid collected in the collection chamber.

In some implementations, the air sampling system may further include a notification unit for generating signals representing notifications indicating detection of one or more target analytes in the liquid collected in the collection chamber.

In another aspect, the present disclosure describes an air sampling system. The air sampling system includes: an air intake unit defining an inlet and an air inflow channel; a fan configured to cause air in a sampling environment to flow into the air inflow channel via the inlet; a cooling unit for cooling air in the air inflow channel; a collection chamber for collecting liquid water condensed from air in the air inflow channel, the collection chamber being removably coupled to the air intake unit and including an active target substrate having a surface that is coated with bioreceptors; and an optical detection unit including a light source, the optical detection unit being configured to illuminate the active target substrate with the light source.

In some implementations, the collection chamber may be coupled to the air intake unit using a threaded connection.

In some implementations, the light source may be an infrared light emitter.

In some implementations, the air sampling system may further include a flow column that is centrally disposed inside the collection chamber, the flow column being fluidly connected to the air inflow channel and defining a plurality of apertures through which fluid flows into the collection chamber.

In some implementations, the air sampling system may further include a plurality of glass beads disposed in an annular space between the flow column and an inner wall of the collection chamber, the surfaces of the plurality of glass beads being exposed to liquid that collects in the collection chamber.

In some implementations, the collection chamber may include a plurality of glass beads disposed in an annular space between the flow column and an inner wall of the collection chamber and the surfaces of the plurality of glass beads may be exposed to liquid that collects in the collection chamber.

In some implementations, the collection chamber may include a permeable stopper that supports the plurality of glass beads above and in spaced relation to a bottom wall of the collection chamber, and the active target substrate may be disposed in a reaction compartment defined by the stopper and the bottom wall of the collection chamber.

In some implementations, the air sampling system may further include an air outflow channel that is fluidly connected to the collection chamber, and the cooling unit may be further configured to cool air in the air outflow channel.

In some implementations, the cooling unit may include one or more cold plates disposed downstream of the inlet, the one or more cold plates being supported in thermal contact with at least a portion of the air inflow channel.

In some implementations, the bioreceptors may be antibodies.

In some implementations, the air sampling system may further include: a liquid inflow channel having a liquid inflow port, the liquid inflow channel being fluidly connected to the collection chamber; a liquid outflow channel that is fluidly connected to the collection chamber; and a liquid pump for causing liquid to flow into and out of the collection chamber.

In some implementations, the air sampling system may further include a flow sensor associated with at least one of the liquid inflow channel or the liquid outflow channel for measuring a rate of flow of liquid out of the collection chamber, and the cooling unit may be controlled based on measurements obtained from the flow sensor.

In some implementations, the air sampling system may further include a sensing unit for determining a volume of liquid in the collection chamber, and the cooling unit may be controlled based on signals generated by the sensing unit.

In some implementations, the sensing unit may be a level sensor associated with the collection chamber.

In some implementations, the cooling unit may be controlled based on determining, from signals generated by the level sensor, whether a liquid level in the collection chamber deviates from a defined level.

In some implementations, the optical detection unit may include optical components for detecting light reflected by the active target substrate and the control parameters of the light source may be adjustable based on a choice of the bioreceptors that are associated with the active target substrate.

In some implementations, the active target substrate may be resin that is treated with the bioreceptors.

In another aspect, the present disclosure describes a liquid collection chamber for an air sampling system. The liquid collection chamber includes: a container for collecting liquid water condensed from air that is drawn into the air sampling system, the container being removably coupled to an air intake unit of the air sampling system; an active target substrate having a surface that is coated with bioreceptors; and a target holder for holding the active target substrate in fluid contact with the liquid in the liquid collection chamber.

In some implementations, the liquid collection chamber may include a flow column that is centrally disposed inside the liquid collection chamber, the flow column being fluidly connected to the air intake unit and defining a plurality of apertures through which fluid flows into the liquid collection chamber.

In some implementations, the liquid collection chamber may include a plurality of glass beads disposed in an annular space between the flow column and an inner wall of the liquid collection chamber and the surfaces of the plurality of glass beads may be exposed to liquid that collects in the liquid collection chamber.

In some implementations, the liquid collection chamber may include a permeable stopper that supports the plurality of glass beads above and in spaced relation to a bottom wall of the liquid collection chamber, and the active target substrate may be disposed in a reaction compartment defined by the stopper and the bottom wall of the liquid collection chamber.

In another aspect, the present disclosure describes a system for real-time detection of airborne pathogens. The system includes: an air intake unit defining an inlet and an air inflow channel; a fan configured to cause air in a sampling environment to flow into the air inflow channel via the inlet; a cooling unit for cooling air in the air inflow channel; a collection chamber for collecting liquid water condensed from air in the air inflow channel, the collection chamber including: an active target substrate having a surface that is coated with bioreceptors; and a reference target substrate that is not coated with bioreceptors, and an optical detection unit that is configured to independently illuminate the active target substrate and the reference target substrate with light for detecting presence of an airborne pathogen.

In some implementations, the optical detection unit may include at least one light source that is directed at the active target substrate and the reference target substrate.

In some implementations, the at least one light source may be an infrared laser.

In some implementations, the optical detection unit may include a laser light bandpass filter.

In some implementations, the at least one light source may be pulse modulated at a frequency that is dependent on the bioreceptors.

In some implementations, the optical detection unit may include: a detector; and a focusing lens that filters light from the at least one light source onto the detector.

In some implementations, the optical detection unit may be configured to illuminate the reference target substrate at different points in time and detect differential measurement of reflected light.

In some implementations, the system may further include a flow column that is centrally disposed inside the collection chamber, the flow column being fluidly connected to the air inflow channel and defining a plurality of apertures through which fluid flows into the collection chamber.

In some implementations, the system may further include a plurality of glass beads disposed in an annular space between the flow column and an inner wall of the collection chamber, the surfaces of the plurality of glass beads being exposed to liquid that collects in the collection chamber.

In some implementations, the system may further include a permeable stopper that supports the plurality of glass beads above and in spaced relation to a bottom wall of the collection chamber, and the active target substrate and the reference target substrate may be disposed in a reaction compartment defined by the stopper and the bottom wall of the collection chamber.

In some implementations, the system may further include an air outflow channel that is fluidly connected to the collection chamber, and the cooling unit may be further configured to cool air in the air outflow channel.

In some implementations, the system may further include an air pump for drawing air out of the collection chamber via the air outflow channel.

In some implementations, the cooling unit may include one or more cold plates disposed downstream of the inlet, the one or more cold plates being supported in thermal contact with at least a portion of the air inflow channel.

In some implementations, the one or more cold plates may be made of aluminum.

In some implementations, the bioreceptors may be antibodies.

In some implementations, the system may further include: a liquid inflow channel having a liquid inflow port, the liquid inflow channel being fluidly connected to the collection chamber; a liquid outflow channel that is fluidly connected to the collection chamber; and a liquid pump for causing liquid to flow into and out of the collection chamber.

In some implementations, the system may further include a sensing unit for determining a volume of liquid in the collection chamber, and the cooling unit may be controlled in response to signals generated by the sensing unit.

In some implementations, the sensing unit may be a level sensor associated with the collection chamber.

In some implementations, the cooling unit may be controlled based on determining, from signals generated by the level sensor, whether a liquid level in the collection chamber deviates from a defined level.

In some implementations, the active target substrate may be resin that is treated with the bioreceptors.

In another aspect, the present disclosure describes a method for detecting airborne pathogens. The method includes: sampling air by drawing air from an ambient environment into an air sampling system; causing condensation of the air into liquid water which collects in a collection chamber; exposing an active target substrate containing a bioreceptor to the liquid collecting in the collection chamber; removing liquid from the collection chamber; introducing liquid containing bioreceptors into the collection chamber; removing the liquid containing bioreceptors from the collection chamber; and performing optical detection operations in connection with the active target substrate for detecting presence of an airborne pathogen.

In some implementations, the method may further include directing light at a reference target substrate in the collection chamber at different points in time and detecting differential measurement of reflected light.

Other example embodiments of the present disclosure will be apparent to those of ordinary skill in the art from a review of the following detailed descriptions in conjunction with the drawings.

The present application discloses an air sampling system. The disclosed system is configured to continuously monitor the air of an indoor environment to detect the presence of one or more particles in the air. More specifically, the air sampling system is configured to detect, in real-time, the presence of airborne pathogens, such as bacteria, fungi, viruses, pollen or other allergens. The air sampling system operates based on condensation of water vapor in sampled air for collection of airborne viruses in condensed liquid water. The air sampling system continuously draws air from the sampling environment and directs the air to an air inflow channel. The air inflow channel is oriented substantially vertically, allowing fluid movement in a downward direction. The air sampling system includes a cooling unit for cooling air in the air inflow channel and a collection chamber. The cooling unit is controlled to cause condensation of the air in the air inflow channel, and the collection chamber collects liquid water that is condensed from the air. That is, the cooling unit causes water vapor in the sampled air to condense into liquid droplets which collect in the collection chamber. In this way, the collected liquid can be analyzed to detect for presence of pathogens.

The air sampling system also includes one or more sensors to facilitate maintaining a consistent volume of liquid in the collection chamber. In particular, the air sampling system maintains a constant volume (or a volume within a defined range) of liquid water in the collection chamber during an air sampling phase, to facilitate collection of sufficient and/or desired quantity of analyte(s) of interest in the collection chamber. The air sampling system may, for example, include various sensors, such as a level sensor, a temperature sensor, and flow rate sensor, for obtaining measurements relating to the volume of liquid water collecting in the collection chamber. A controller associated with the air sampling system can determine, based on the measurements obtained from the various sensors, whether to increase or decrease the liquid level in the collection chamber, and control the cooling unit accordingly for cooling the sampled air. For example, the controller may determine if the liquid level deviates from a defined threshold (or range) of volume and adjust the cooling unit to rectify the deviation (e.g. increasing or decreasing the temperature of the cooling unit). Additionally, or alternatively, the controller may cause other components of the air sampling system 100 to operate differently in order to maintain a consistent volume of liquid in the collection chamber. For example, the controller may adjust operation of the fan to increase a rate of air inflow into the air sampling system 100, which may allow a greater volume of water vapor to be condensed to liquid.

The present application also discloses a liquid collection chamber which may be used with an air sampling system. The liquid collection chamber may, for example, be a removable component of an air sampling system. A liquid collection chamber includes, at least, an active target substrate that is coated with a recognition component, or bioreceptor (e.g. enzyme, antibody, cell, nucleic acid, aptamer, etc.). More generally, the active target substrate may contain a receptor/reagent that is known to react with a specific analyte of interest. The active target substrate is exposed to the liquid solution collected in the liquid collection chamber, such that an analyte in the solution can react with the receptor/reagent. The air sampling system facilitates optical detection of different types of airborne particles, as one liquid collection chamber containing a biomolecular target can be replaced by another liquid collection chamber containing a different biomolecular target. In particular, the liquid collection chamber may be an independent component, such as a replaceable cartridge, that is manufactured separately from the air sampling system. The liquid collection chamber is compatible (i.e. can be operatively coupled) with the air sampling system, and can be replaced after a pathogen of interest is detected and/or if a different analyte of interest is desired to be detected by the air sampling system.

Figure 1A:
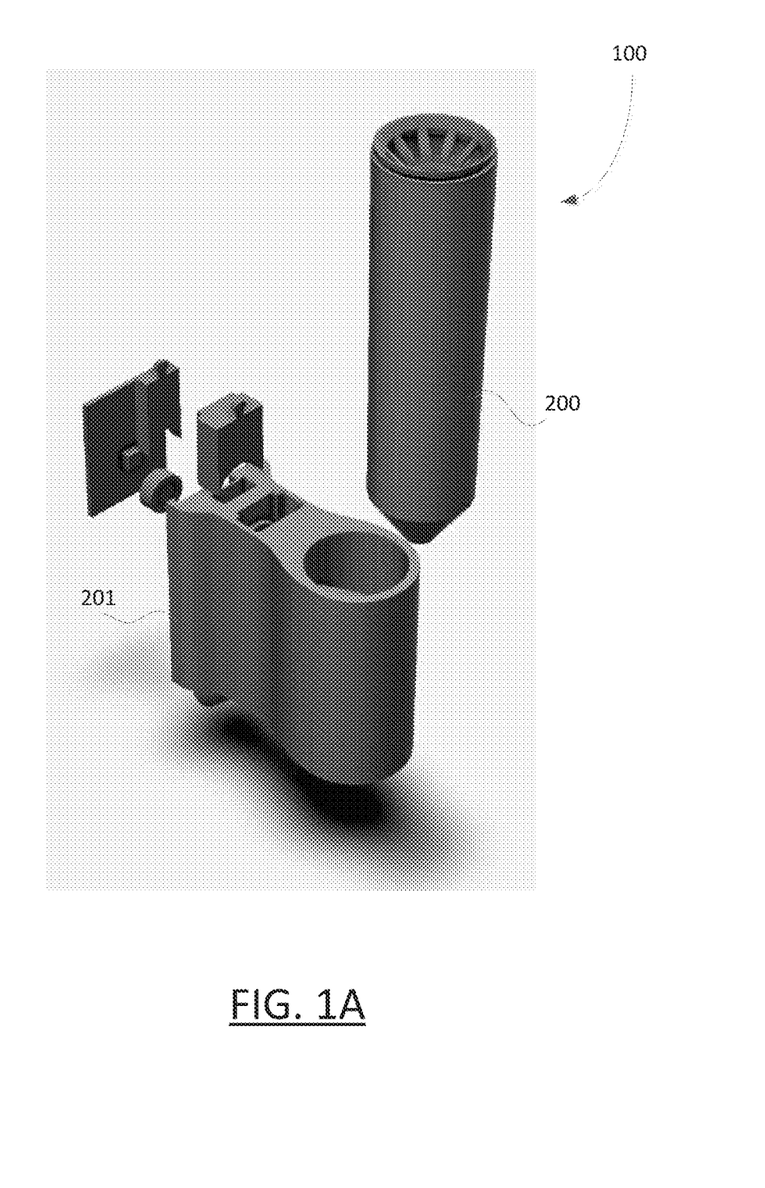
FIG. 1A is a partial exploded view of an example air sampling system, in accordance with embodiments of the present disclosure.

Reference is first made to FIG. 1A which is a partial exploded view of an example air sampling system 100, in accordance with embodiments of the present disclosure. The air sampling system 100 may be used for continuously monitoring air in an indoor environment. FIG. 1A illustrates a collection chamber 200 and an optical detection unit/subsystem 201. The collection chamber 200 is removably coupled to the optical detection unit 201. As will be explained in greater detail below, the collection chamber 200 collects liquid water that is condensed from air sampled from the indoor environment. The collection chamber 200 also includes a reaction compartment in which a target analyte may react with a bioreceptor. The optical detection unit 201 houses optical components that enable the detection of a target analyte inside the collection chamber 200. The collection chamber 200 is replaceable—that is, the collection chamber 200 may be replaced by another collection chamber containing a different bioreceptor, and the optical detection unit 201 may operate in a similar manner to enable detection of a different target analyte. The air sampling system 100 may be portable or fixed in place in an indoor environment. For example, the air sampling system 100 may be mounted on a wall of a room inside a facility and used to monitor the air of the room.

Figure 1B:
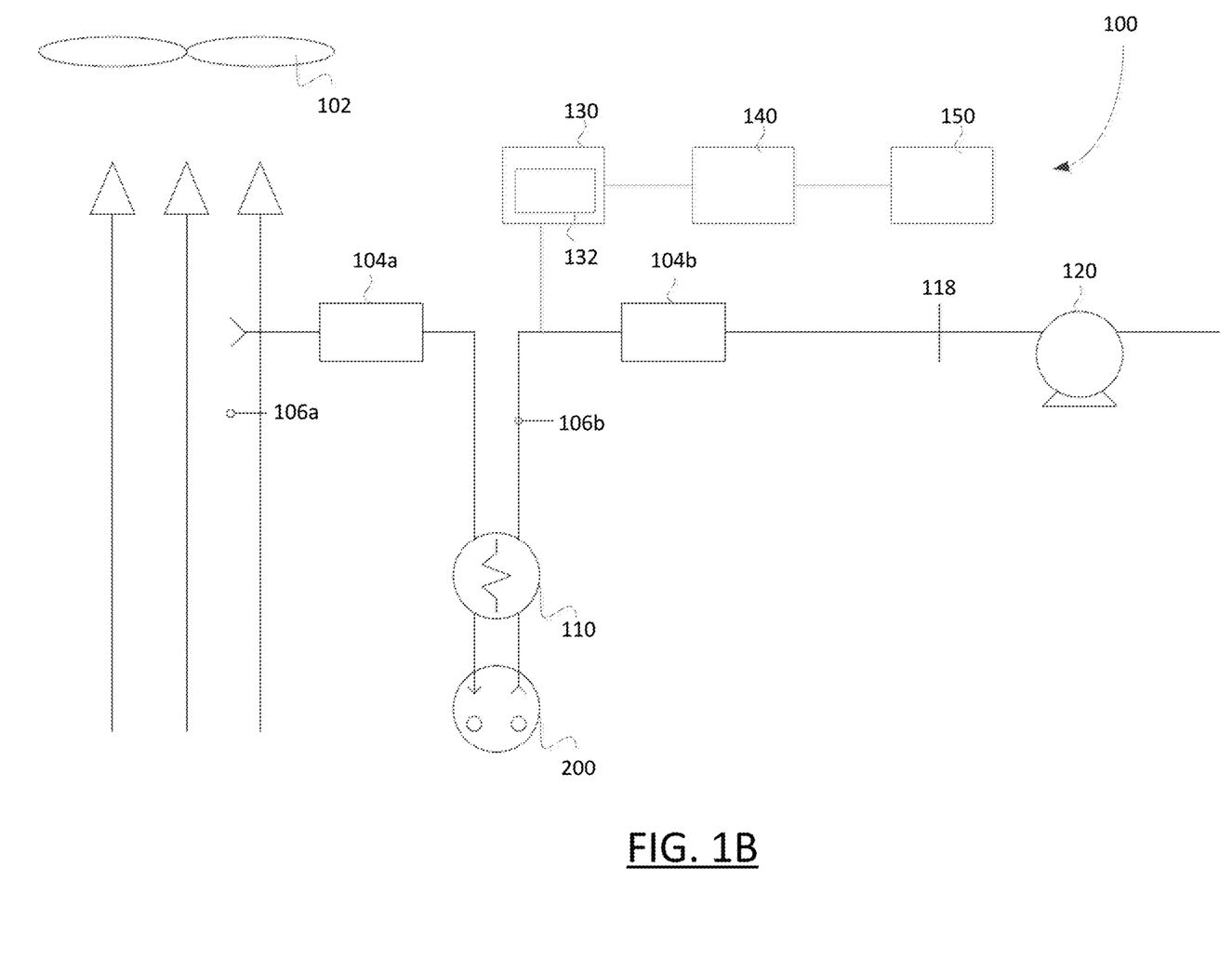
FIG. 1B is a high-level schematic diagram of the example air sampling system of FIG. 1A.

Reference is now made to FIG. 1B which is a high-level schematic diagram of the air sampling system 100. The air sampling system 100 includes a controller 130. The controller is configured to control the overall operation of the air sampling system 100. In at least some embodiments, the controller includes one or more processors, such as microprocessors. The processor is communicably coupled with various devices and subsystems, some of which are illustrated in FIG. 1B.

The air sampling system 100 includes a fan 102, or similar device for creating a flow of air from the sampling environment into the air sampling system 100. The fan 102 helps to circulate air in the sampling environment in order to draw air from different parts of the sampling environment. The fan 102 may be controlled to draw air into the air sampling system 100 on a continuous basis, or at specific times or time intervals. For example, air may be drawn into the air sampling system 100 at defined intervals. As will be explained further below, in some embodiments, the fan 102 may be operated to draw in more air from the sampling environment as needed to increase the liquid level (i.e. more condensation) in the collection chamber 200.

The air sampling system 100 also includes a cooling unit 110. The cooling unit 110 provides localized cooling of air. In particular, the cooling unit 110 is configured to cool the air that is drawn into the air sampling system 100 to cause condensation of water vapor in the air. The temperature of the cooling unit 110 may be varied by a controller of the air sampling system 100.

The collection chamber 200 of the air sampling system 100 is arranged such that it is located substantially vertically below the cooling unit 110. Incoming air in the air sampling system 100 is cooled by the cooling unit 110 to cause condensation of the water vapor in the air. As the air is cooled, airborne particles, or aerosols, combine with condensate droplets to form larger particles that, due to the effect of gravity, drop into and collect in the collection chamber 200.

The air sampling system 100 also includes air particulate monitors 104a and 104b. The air particulate monitors 104a and 104b are used for measuring the particulate matter content (e.g. solid particles such as dust, powder, pellets, etc.) in the ambient air. The air particulate monitors 104a and 104b may be associated with an air inlet and an air outlet, respectively, of the air sampling system 100 such that air being drawn into, as well as air being expelled out of, the air sampling system 100 may be monitored.

The air sampling system may include temperature and humidity sensors 106a and 106b at an air inlet and an air outlet, respectively. In at least some embodiments, the temperature and humidity sensors 106a and 106b may be used for obtaining measurements that is used for controlling the cooling unit 110. For example, the temperature and/or humidity of incoming air may be measured, and the controller may vary a temperature of the cooling unit 110 based on the measurements obtained from the temperature and/or humidity sensors.

The air sampling system may also include one or more air pumps 120 for drawing air out of the air sampling system 100. The air may be expelled through an exhaust and back into the sampling environment. The air pump 120 may, for example, be a high-volume sampling pump. The air sampling system may also include a hygroscopic filter 118, which removes moisture and particles from the air.

The air sampling system 100 may also include a communication subsystem (not shown in FIG. 1B) which allows the air sampling system 100 to communicate over a wireless network. The communication subsystem may include, at least, a receiver, a transmitter, and associated components, such as one or more antenna elements, local oscillators (LOs), and a processing module such as a digital signal processor (DSP). The antenna elements may be embedded or internal to the air sampling system 100 and a single antenna may be shared by both receiver and transmitter. The particular design of the wireless communication subsystem may depend on the wireless network in which the air sampling system 100 is intended to operate.

The air sampling system 100 may also include a notification module/unit 132. The notification unit may generate signals representing notifications indicating detection of one or more target analytes in the air sampling system 100. More particularly, if a target analyte is detected in liquid that is collected in the collection chamber 200, the notification unit of the air sampling system 100 may generate notifications of the detection. For example, a notification, such as a visual or auditory alert or message, may be displayed on a display device associated with the air sampling system 100, or transmitted wirelessly to one or more computing devices via a wireless network (e.g. over Wi-Fi, Bluetooth, etc.). The notification unit may also generate notifications relating to operation of the air sampling system 100. For example, a controller associated with the air sampling system 100 may determine that the collection chamber 200 should be replaced, for example, after a pathogen is detected by the air sampling system 100 or if the particulate matter content of the sampled air or collected liquid in the air sampling system 100 is determined to fall outside an acceptable level/range. The controller may then cause the notification unit to generate and provide notifications to an operator of the air sampling system 100 to replace the collection chamber 200.

Figure 2:
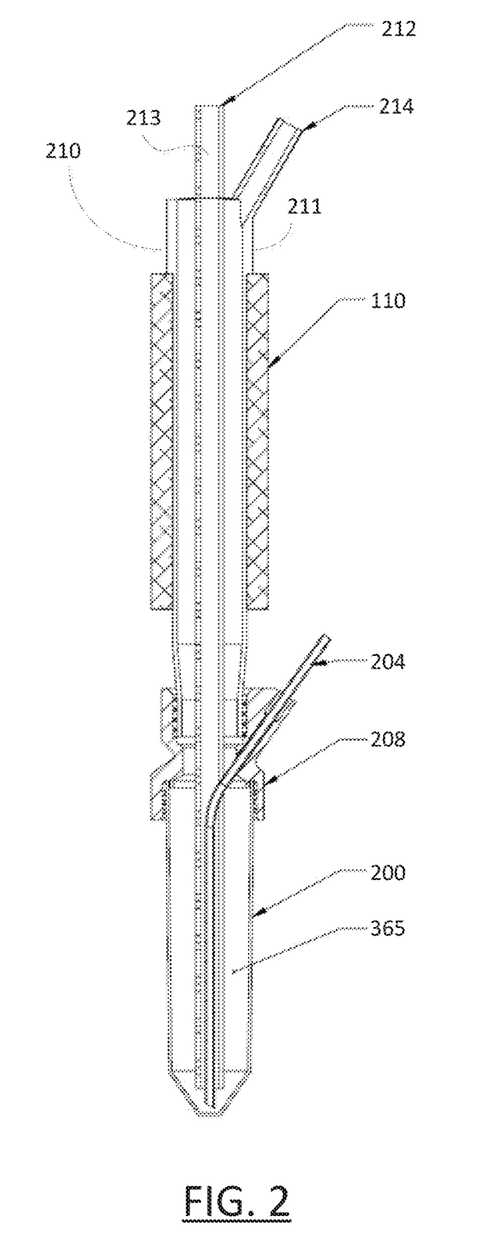
FIG. 2 is a partial side cross-sectional view of internal components of the example air sampling system of FIG. 1A.

Reference is now made to FIG. 2 which is a partial side cross-sectional view of internal components of the air sampling system 100. FIG. 2 illustrates an example arrangement of internal components; it will be understood that different arrangements and additional internal components may be possible. The air sampling system 100 includes an air intake unit 210 that is fluidly connected to the collection chamber 200. The air intake unit 210 facilitates flow of air from the ambient environment into the air sampling system 100. As shown in FIG. 2, the air intake unit 210 defines an inlet 212 and an air inflow channel 213. The inlet 212 is located at a top end of the air inflow channel 213. The air inflow channel 213 defines an airflow passageway (or path) into the air sampling system 100. Ambient air enters the air inflow channel 213 via the inlet 212. For example, the fan 102 may be configured to cause ambient air to flow into the air inflow channel 213. In at least some embodiments, the air inflow channel 213 is substantially vertically oriented. That is, inflowing air moves substantially in a downward direction within the air inflow channel 213.

The air intake unit 210 may, in some embodiments, include a tubular member or vessel that defines the air inflow channel 213. As shown in FIG. 2, the air intake unit 210 may include a housing 211 and the air inflow channel 213 may be a tubular member that extends through the housing 211. The tubular member may be elongate and extend from the air intake unit 210 at least partially into the collection chamber 200. In particular, the air inflow channel 213 is fluidly connected with the collection chamber 200, such that fluids (e.g. air, condensed liquid water) flowing through the air inflow channel 213 enter the collection chamber 200 due to gravity.

In at least some embodiments, the collection chamber 200 is removably coupled to the air intake unit 210. That is, the collection chamber 200 can be operatively coupled with the air sampling system 100 and can also be removed from the air sampling system 100 (e.g. by detaching). For example, the collection chamber 200 may be coupled to the air intake unit 210 using a threaded connection. In FIG. 2, a coupler component 208 is used to connect a housing 211 of the air intake unit 210 with the collection chamber 200. The coupler component 208 may be affixed to the housing 211 and the collection chamber 200 may be removably connected to the coupler component 208. The coupler component 208 may itself be a separate component that is independent of and compatible with the air sampling system 100. In some other embodiments, the collection chamber 200 may be directly coupled to the housing 211 (i.e. without an intermediary coupler component). Various different coupling mechanisms may be used for operatively connecting the collection chamber 200 to the air sampling system 100. the collection chamber 200 can be removed from the air sampling system 100 and replaced by another collection chamber. For example, a collection chamber containing a different analyte of interest may be operatively coupled to the air sampling system 100. In this way, the air sampling system 100 can be used for various different purposes (e.g. detection of a different analyte in the ambient air, etc.), or for the same purpose for a prolonged period of time (e.g. by replacing the collection chamber with a new one).

The air sampling system 100 also includes an air outflow channel 214. Ambient air that enters the air sampling system 100 via the air inflow channel 213 passes through the collection chamber 200 and is subsequently expelled from the air sampling system 100 via the air outflow channel 214. In particular, the air outflow channel 214 is fluidly connected to the collection chamber 200. As shown in FIG. 2, in some embodiments, the air outflow channel 214 may be oriented substantially vertically.

The air sampling system 100 includes a cooling unit 110. In the example embodiment of FIG. 2, the cooling unit 110 comprises one or more cold plates that are disposed downstream of the inlet 212. The cold plates may, for example, be made of aluminum. The cooling unit 110 is mounted to the housing 211 of the air intake unit 210. In at least some embodiments, the cooling unit (e.g. cold plates) may be supported in thermal contact with at least a portion of the air inflow channel. In FIG. 2, the cooling unit 110 extends vertically along the housing 211, covering a defined length of the air inflow channel 213. The cooling unit 110 is configured to cool air passing through at least a portion (e.g. a covered length) of the air inflow channel 213. In particular, the cooling unit 110 may be controlled (for example, by a controller of the air sampling system 100) to cause condensation of the water vapor in the air passing through at least a portion of the air inflow channel 213. The controller varies the temperature of the cooling unit 110. In at least some embodiments, the temperature of the cooling unit 110 may be varied in order to maintain a desired volume of liquid water in the collection chamber 200. As air passes in the air inflow channel 213, the cooling unit 110 causes water droplets to form due to condensation. By varying the temperature of the cooling unit 110, the volume of liquid collecting in the collection chamber 200 can be controlled. For example, a minimum level of liquid may be maintained in the collection chamber 200 by monitoring and controlling the temperature of the cooling unit 110.

In some embodiments, the cooling unit 110 may be configured to cool air passing through the air outflow channel 214. More specifically, the air that is removed from the collection chamber 200 via the air outflow channel 214 may be cooled by the cooling unit 110. For example, the warmer, drier air inside the collection chamber 200 may absorb some of the liquid water in the collection chamber 200 and reduce the volume of collected liquid. To prevent a variance in liquid level, the air flowing out from the collection chamber 200 may be cooled to remove (i.e. via condensation) liquid that has been absorbed.

In at least some embodiments, the air sampling system 100 includes a sensing unit 140 for determining a volume of liquid in the collection chamber 200, and the cooling unit 110 may be controlled in response to signals generated by the sensing unit. For example, the sensing unit may be a level sensor associated with the collection chamber 200. The level sensor may, for example, be a capacitive sensor. Based on signals generated by the level sensor, the controller of the air sampling system 100 may determine whether a liquid level in the collection chamber 200 deviates from a defined threshold level. For example, the controller may detect if the liquid level is above or below a defined threshold (or a range of volume defined by lower and upper limit values). If the liquid level falls below the threshold, the temperature of the cooling unit 110 may be varied to allow more liquid to condense from the inflowing air. For example, the controller may lower the temperature of the cooling unit 110 to increase the rate of condensation in the air inflow channel 213. Additionally, or alternatively, the fan 102 of the air sampling system 100 may be caused to increase air flow into the air inflow channel 213.

The air sampling system 100 may include other sensors, such as a temperature sensor, a humidity sensor, a liquid flow sensor etc. which may be used for maintaining a desired volume of liquid (i.e. a defined level or range of volume) in the collection chamber 200. In particular, the cooling unit 110 may be controlled based on measurements obtained from one or more of these sensors. By continuously monitoring the temperature, humidity, flow rates, etc., the air sampling system 100 is configured to maintain a substantially constant level of liquid corresponding to a desired solution volume for detection of a target analyte.

The air sampling system 100 includes a liquid inflow channel 204 having a liquid inflow port. The liquid inflow channel 204 is fluidly connected to the collection chamber 200. The air sampling system 100 also includes a liquid outflow channel. In some embodiments, the liquid inflow channel 204 and the liquid outflow channel may be the same structural component. That is, liquid may flow into and out of the collection chamber 200 via the same flow channel. For example, a liquid pump 150 may cause liquid to flow into and out of the collection chamber 200. As will be described in greater detail below, various liquid solutions may be introduced into the collection chamber 200 via the liquid inflow channel 204. The solutions may subsequently be removed using the same flow channel or a separate liquid outflow channel. In at least some embodiments, the liquid inflow channel 204 and the liquid outflow channel may be fluidly connected to the reaction compartment. For example, an outlet opening of the liquid inflow channel 204 (and inlet opening of the liquid outflow channel) may be located adjacent to or inside the reaction compartment, such that liquid flowing in the liquid inflow channel 204 enters the reaction compartment directly (and similarly, liquid in the reaction compartment is removed via the liquid outflow channel).

In some embodiments, the air sampling system 100 may include a flow sensor associated with at least one of the liquid inflow channel 204 or the liquid outflow channel. The flow sensor is configured to measure the rate of flow of liquid into and/or out of the collection chamber 200. The cooling unit 110 may, in some embodiments, be controlled based on measurements obtained from the flow sensor(s). In particular, the controller of the air sampling system 100 may determine, based on measurements of the flow sensor(s), whether to vary the temperature of the cooling unit 110 in order to adjust the volume of liquid in the chamber 200.

Figure 3:
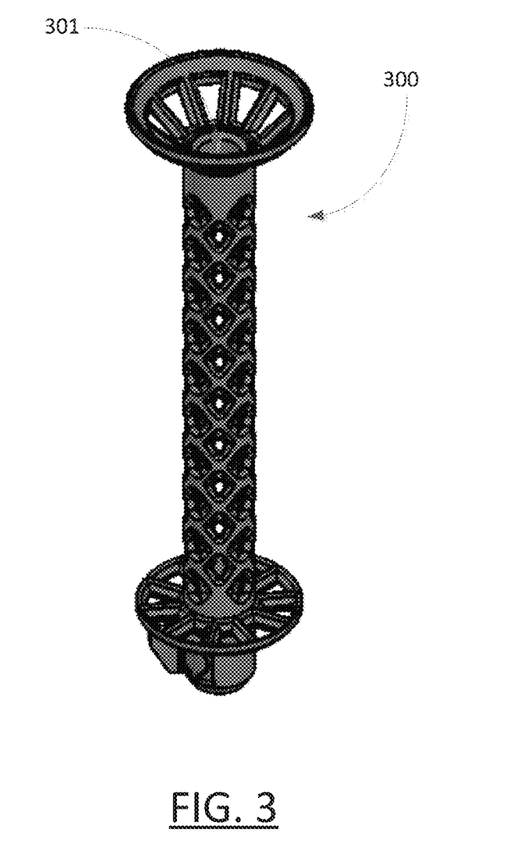
FIG. 3 is a perspective view of an example flow column which may be disposed inside a collection chamber.

The collection chamber 200 of the air sampling system 100 will be described in greater detail with reference to FIGS. 3, 4A-4B, 5A-5B and 6A-6C. In at least some embodiments, the collection chamber 200 includes a flow column. A perspective view of an example flow column 300 is shown in FIG. 3. As shown in FIGS. 6A-6B, the flow column 300 may be centrally disposed inside the collection chamber 200. The flow column 300 is fluidly connected to the air inflow channel 213. In particular, fluid (e.g. air, condensed liquid water) flowing through the air inflow channel 213 may enter an opening 301 defined at a top end of the flow column 300. The flow column 300 also defines a plurality of slots 302 which allow flow of fluid therethrough and into the collection chamber 200. For example, the plurality of slots 302 may allow drainage of condensed liquid water flowing from the air inflow channel 213. In the example embodiment of FIG. 3, the flow column 300 includes a conical top member defining a lip (or flange) 304 and a plurality of slots 302. Other configurations may be possible for providing fluid connection between the air inflow channel 213 and the flow column 300.

Figure 4A:
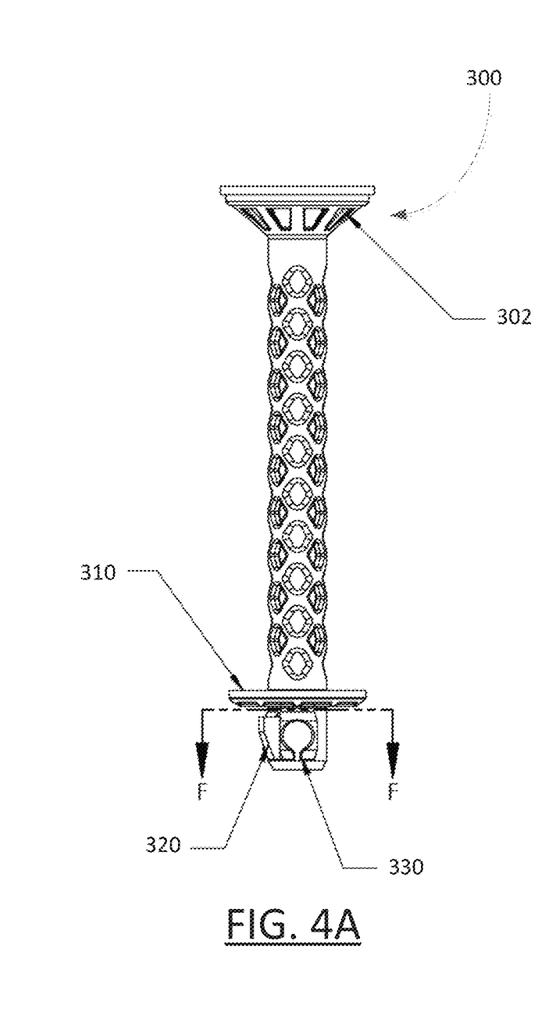
FIGS. 4A and 4B show side views of the example flow column of FIG. 3.
Figure 4B:
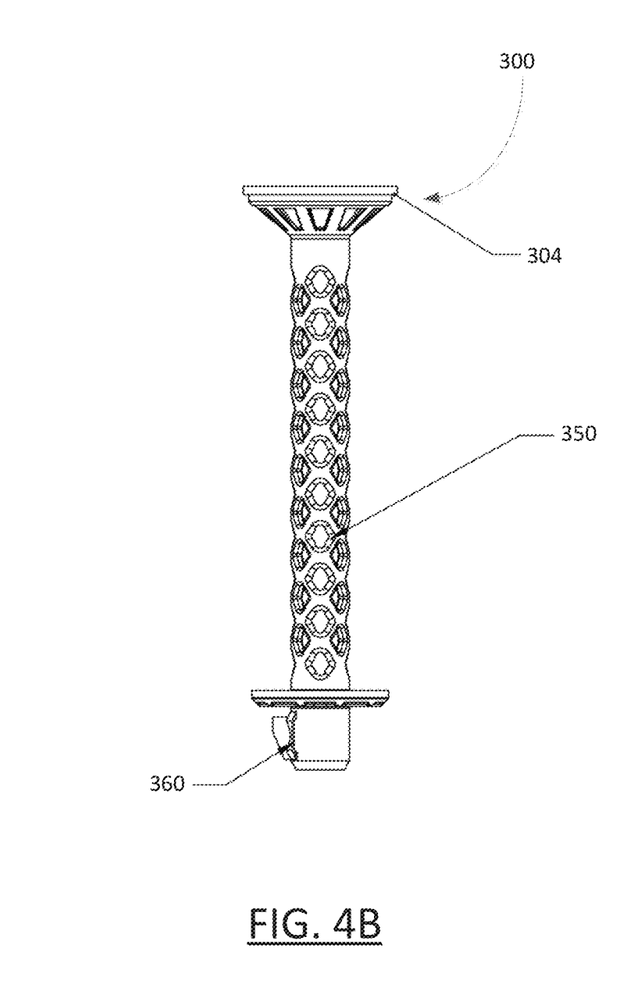

Reference is made to FIGS. 4A and 4B which show side views of the example flow column 300 of FIG. 3. The flow column 300 defines a plurality of apertures 350 along a cylindrical portion of the flow column 300 and a central bore extending through the cylindrical portion. The plurality of apertures 350 allow for fluid movement between the flow column 300 and the collection chamber 200. In particular, liquid water and air can flow through the flow column 300 (for example, in the bore extending through the cylindrical portion) and enter the collection chamber 200 via the apertures 350. As the flow column 300 is disposed inside the collection chamber 200, the fluid in the collection chamber 200 may flow into and out of the flow column 300 through the apertures 350.

The collection chamber 200 allows for detection of one or more analytes in the liquid solution that collects in the collection chamber 200. For a given analyte of interest, the collection chamber 200 includes at least one substrate containing a reagent/receptor that is known to react with the analyte. More particularly, the collection chamber 200 includes an active target substrate having a surface that is at least partly coated with bioreceptors. In at least some embodiments, the bioreceptors may be antibodies which may interact and bind with antigens of a given pathogen. For example, the bioreceptors may be antibodies for a given target virus. The active target substrate may, in some embodiments, be a piece of resin that is treated with a receptor/reagent. The receptor serves as a selective "glue" that allows an analyte of interest to bind to the receptor (and the active target substrate) while other particles will not.

The active target substrate may be located at a bottom portion of the collection chamber 200. In particular, the active target substrate may be included in (or coupled to) the flow column 300 inside the collection chamber 200. For example, the active target substrate may be inserted into a slot 360 that is defined at a bottom portion of the flow column 300. The active target substrate may, for example, be positioned below the plurality of apertures 350 defined on the flow column 300.

In some embodiments, the collection chamber 200 may additionally include a reference target substrate. The reference target substrate is not coated with any receptor/reagent. The reference target substrate may, for example, be a piece of resin. As will be explained further below, a reference target substrate may allow the air sampling system 100 to account for the presence of contaminants in the sampled ambient air. In particular, the reference target substrate allows for cancelling out the optical effects (during an analyte detection phase) that are caused by contaminants different from the analyte of interest.

Reference is made to FIGS. 6A and 6B which show side cross-sectional views of a collection chamber 200 of the air sampling system 100. In at least some embodiments, the air sampling system 100 includes a plurality of glass beads 390 that are disposed inside the collection chamber 200. The surfaces of the plurality of glass beads are exposed to liquid that collects in the collection chamber 200. During an analyte detection phase, the inflowing air from the ambient environment is caused to "bubble" through the liquid collected in the collection chamber 200. This "bubbling" refers to the forced movement of air, in which one or more contaminants may be dissolved or suspended, through a liquid solution. The forced movement may be effected, for example, through the use of an air pump or other air transferring device. By bubbling the inflowing air through the liquid in the collection chamber 200, particles of an analyte of interest may be scrubbed out into the liquid solution. The glass beads 390 in the collection chamber 200 may be useful for preventing re-aerosolization of such particles that are removed through the bubbling process. For example, re-aerosolization of virus particles into air outflowing from the collection chamber 200 is harmful and frustrates the virus detection process of the air sampling system 100. By increasing the reaction surface area between the glass beads 390 and the liquid media, re-aerosolization of the removed particles may be prevented or reduced.

FIGS. 6A and 6B show that the glass beads 390 may be positioned between the flow column 300 and the inner wall of the collection chamber 200. More specifically, the flow column 300 and the collection chamber 200 may define an annular space 365, and the glass beads 390 may fit in the annular space 365. The fluid flowing from the air intake unit 210 and/or the air inflow channel 213 into the collection chamber 200 may move in the annular space 365 through gaps between the glass beads 390. In particular, fluid may flow through the apertures 350 defined on the flow column 300 and between the glass beads 390. The glass beads 390 may have different sizes, or they may all have a uniform size. In at least some embodiments, the size of the apertures 350 may be smaller than the cross-sectional area of the glass beads 390, which prevents the glass beads 390 from entering the interior of the flow column 300 through the apertures 350. That is, the apertures 350 may be sized so as to ensure that the glass beads 390 are disposed in the space between (outer wall of) the flow column 300 and the inner wall of the collection chamber 200. For example, the glass beads 390 may be disposed against the exterior side of the flow column 300, without covering the apertures 350. The glass beads 390 may, for example, be supported at a defined distance away from the apertures 350, or may be shaped so as not to fittingly engage the apertures 350.

Figure 6A:
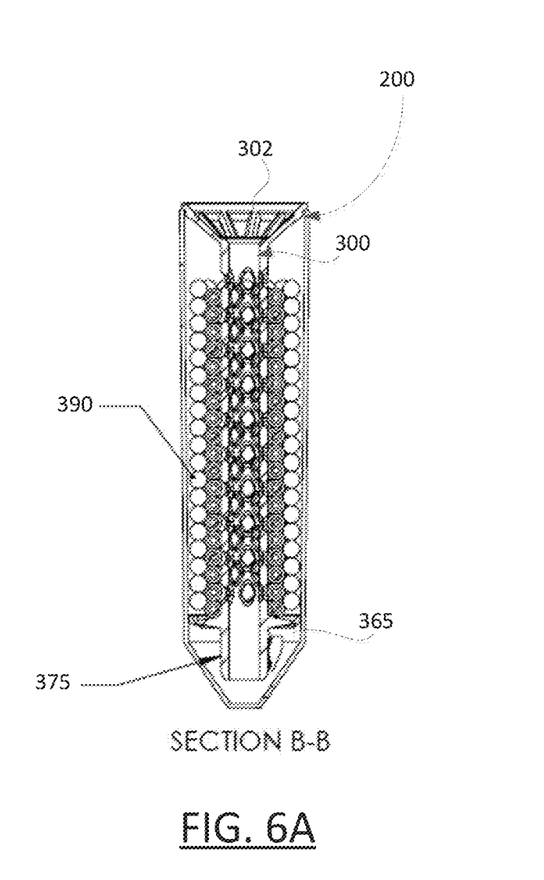
FIGS. 6A and 6B show side cross-sectional views of a collection chamber of the example air sampling system of FIG. 1A.
Figure 6B:
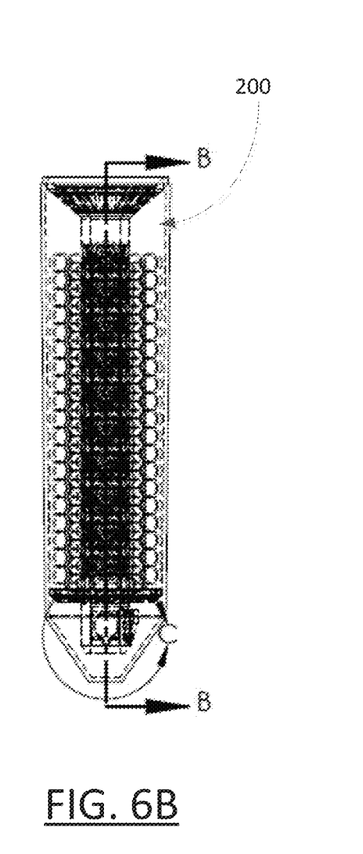
Figure 6C:
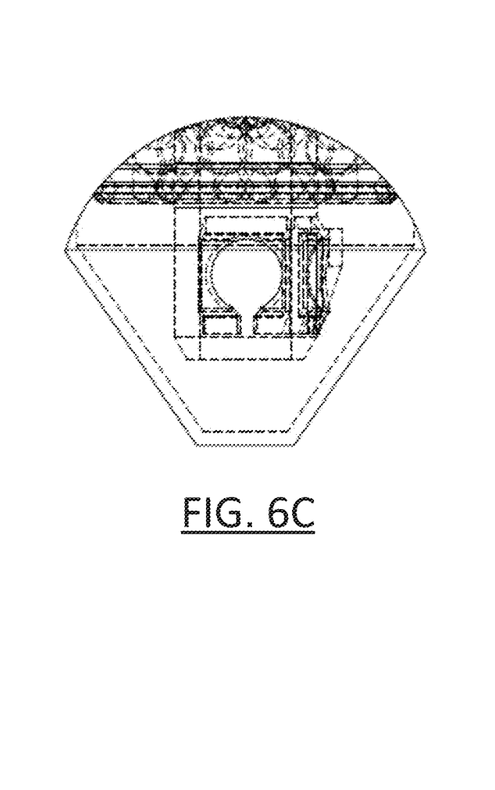
FIG. 6C shows a magnified view of a reaction compartment inside a collection chamber of the example air sampling system of FIG. 1A.

The air sampling system 100 may also include a permeable stopper 310 that supports the plurality of glass beads 390 above and in spaced relation to a bottom wall of the collection chamber 200. More specifically, the stopper 310 maintains the glass beads 390 a predetermined distance away from the bottom of the collection chamber 200. The stopper 310 and the bottom wall of collection chamber 200 define a space—a reaction compartment—in which the active target substrate is disposed. The reaction compartment is a space located at a bottom portion of the collection chamber 200 where an analyte of interest is allowed to interact with a receptor/reagent. The stopper 310 ensures that the glass beads 390 are maintained above and out of the reaction compartment. FIG. 6C shows a magnified view of a reaction compartment inside the collection chamber 200. The stopper 310 is permeable, such that fluid flowing in an upper portion of the collection chamber 200, including ambient air, condensed liquid water, and liquid solution in the collection chamber 200, reaches the reaction compartment. The stopper 310 may, for example, define a plurality of openings through which fluid can flow into the reaction compartment. The openings may be sized so as to prevent any of the glass beads 390 from entering the reaction compartment. In particular, the fluid movement allows for the analyte in the liquid solution to react with the receptor/reagent on the active target substrate.

Figure 5A:
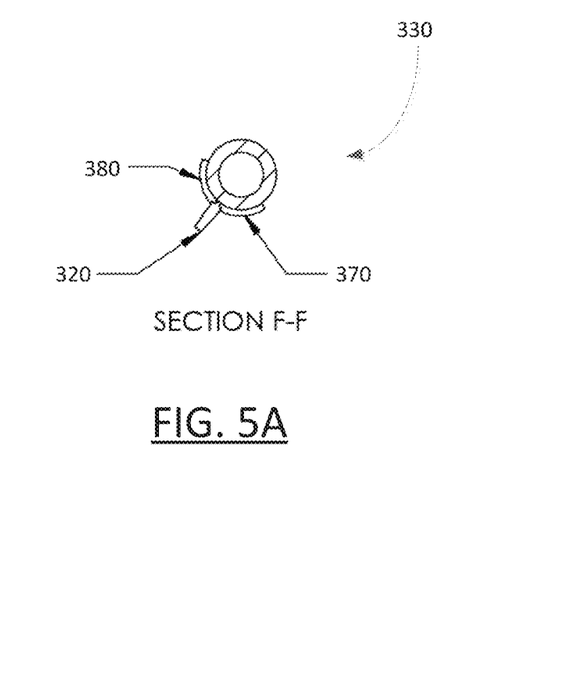
FIG. 5A is a sectional view of a target holder inside a collection chamber of the example air sampling system of FIG. 1A.
Figure 5B:
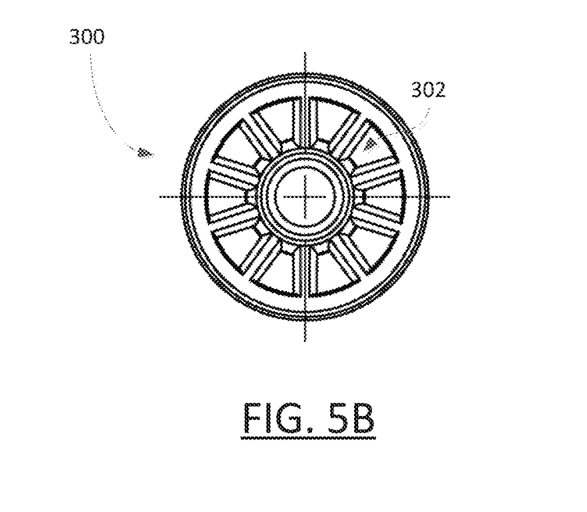
FIG. 5B is a top view of the example flow column of FIG. 5.

FIG. 5A shows an example target holder 330 which may be located in the reaction compartment of the collection chamber 200. The target holder 330 supports at least an active target substrate 370. In particular, the target holder 330 supports the active target substrate 370 in fluid contact with the liquid in the collection chamber 200. The condensed liquid water is allowed to flow into the reaction compartment and the target holder 330 exposes the active target substrate 370 to the liquid water. In the example of FIG. 5A, the target holder 330 additionally supports a reference target substrate 380, and includes a divider 320 for isolating the optical effects of one of the active target substrate 370 and the reference target substrate 380 from the other.

As illustrated in FIG. 1A, the air sampling system 100 includes an optical detection unit 201 that is removably coupled to the collection chamber 200. The optical detection unit 201 houses various optical components that allow for detection of particles in the liquid solution collected in the collection chamber 200. In particular, the optical detection unit 201 is configured to independently illuminate the active target substrate 370 and the reference target substrate 380 using a light source. The light source may, for example, be an infrared laser. The optical detection unit 201 may include one or more bandpass filters, such as a laser light bandpass filter. The optical detection unit 201 includes a detector, such as an infrared detector, and a focusing lens that filters light from the light source onto the detector. The light source may be pulse modulated at a frequency that is dependent on the receptors and/or analyte of interest.

Figure 7:
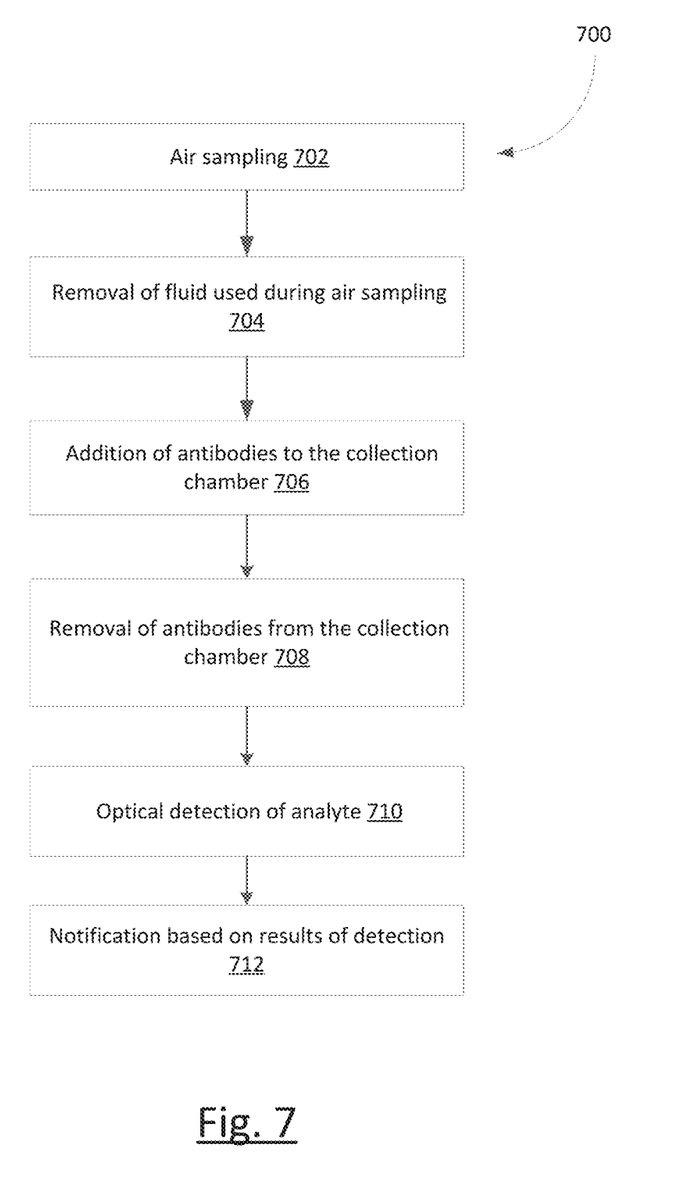
FIG. 7 shows, in flowchart form, an example method for detecting airborne pathogens.

Reference is now made to FIG. 7 which shows, in flowchart form, an example method 700 for detecting airborne pathogens. The method 700 may be performed by an air quality monitoring system, such as the air sampling system 100 of FIG. 1. More particularly, the operations of method 700 may be performed by a controller (which may include one or more processors) of the air sampling system 100.

In operation 702, air from an ambient environment is sampled. The ambient air is collected by the air sampling system by, for example, operating a fan to cause air to flow into an air intake unit (i.e. air inflow channel) associated with the air sampling system. The inflowing air passes through a cooling unit, which causes condensation of the water vapor in the air to liquid form. The controller can vary the temperature of the cooling unit to cause a desired volume of liquid to be condensed from the inflowing air. The collection chamber initially contains only a saline solution, and the particulate matter (e.g. dirt, virus, etc.) in the sampled air is added to the liquid solution in the collection chamber.

In at least some embodiments, the inflowing air may be bubbled through the saline solution in the collection chamber, in order to trap the analyte of interest in the liquid (or "analyte solution") and to allow the analyte in the liquid to react with the active target substrate in the reaction compartment of the collection chamber. The inflowing air may be bubbled for a predetermined period of time. The analyte solution is subsequently pumped out of the collection chamber, in operation 704, and a wash of cleaning solution (e.g. distilled water) is flushed through the collection chamber. A liquid inflow/outflow channel may be used for removing the analyte solution from and introducing the cleaning solution into the collection chamber. In particular, the analyte solution is drawn out from the reaction compartment of the collection chamber. The volume of cleaning solution used may be just enough to cover the targets (i.e. active target substrate and optionally, reference target substrate) that are located in the reaction compartment.

In operation 706, a liquid solution containing a receptor/reagent (or "reagent solution") that is known to react with the analyte of interest is introduced into the collection chamber. The receptor/reagent may, for example, be antibodies for a virus that is being monitored by the air sampling system. The specific receptor/reagent used in the reagent solution depends on the analyte being detected. The volume of reagent solution used may be just enough to cover the targets. In particular, the volume of reagent solution may be less than the volume of liquid solution used during the air sampling phase—the receptor/reagent only needs to cover the active (and optionally, reference) target substrates.

The reagent solution is removed from the collection chamber, in operation 708, and an optical detection operation 710 follows. During optical detection, a light source, such as an infrared laser, is directed at the active target (and reference target) substrate. The light directed at the target is modulated at a particular frequency, which depends on the specific analyte of interest and receptor used in the detection. The light serves as an excitation source for the analyte/receptor, causing proteins on the surface of the analyte/receptor to vibrate. The spectrum of light that bounces off the analyte/receptor can be detected and analyzed to identify the specific analyte of interest. For example, for a given analyte/receptor combination, an optical detection unit of the air sampling system may monitor for light that has a specific frequency. In some embodiments, a bandpass filter may be used in conjunction with the light source, and a focusing lens may filter the reflected light onto a detector. If reflected light of a specific frequency is detected, the analyte of interest may be determined to be present on the active target substrate. Upon detection of the analyte, the controller may cause notifications to be generated based on the results of the detection, in operation 712.

In at least some embodiments, the light source of the optical detection unit may also direct light at the reference target substrate. Since the sampled air may have contaminants (e.g. dust particles) which can affect analyte detection, the reference target substrate is used to cancel any optical effects resulting from the contaminants. More particularly, a reference target check operation may be performed. This is done by comparing the reference signal from a current measurement of reflected energy by the reference target with the reference signal from an initial measurement of the reflected energy (i.e. measurement of the energy reflected at reference target in the initial setup of the system), to monitor for degradation in measured energy level.

The various embodiments presented above are merely examples and are in no way meant to limit the scope of this application. Variations of the innovations described herein will be apparent to persons of ordinary skill in the art, such variations being within the intended scope of the present application. In particular, features from one or more of the above-described example embodiments may be selected to create alternative example embodiments including a sub-combination of features which may not be explicitly described above. In addition, features from one or more of the above-described example embodiments may be selected and combined to create alternative example embodiments including a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. An air sampling system, comprising:
   an air inflow channel having an air inlet portion at a top end, the air inflow channel being oriented substantially vertically;
   a fan configured to cause air in a sampling environment to flow into the air inflow channel via the inlet portion;
   a cooling unit for cooling air in the air inflow channel, the cooling unit disposed downstream of the inlet portion;
   a collection chamber for collecting liquid water condensed from air in the air inflow channel, the collection chamber being fluidly connected to the air inflow channel;
   a sensing unit for determining a volume of liquid water in the collection chamber; and
   a controller configured to adjust a temperature of the cooling unit based on signals generated by the sensing unit.

2. The air sampling system of claim 1, wherein the sensing unit comprises a level sensor associated with the collection chamber.

3. The air sampling system of claim 2, wherein the level sensor is a capacitive sensor.

4. The air sampling system of claim 2, wherein the controller is configured to control the cooling unit based on determining, from signals generated by the level sensor, whether a liquid level in the collection chamber deviates from a defined level.

5. The air sampling system of claim 1, further comprising an air outflow channel that is fluidly connected to the collection chamber, the air outflow channel being oriented substantially vertically, wherein the cooling unit is further configured to cool air in the air outflow channel.

6. The air sampling system of claim 1, wherein the cooling unit comprises one or more cooling coils disposed downstream of the inlet portion, the one or more cooling coils being supported in thermal contact with at least a portion of the air inflow channel.

7. The air sampling system of claim 1, wherein the cooling unit comprises one or more cold plates disposed downstream of the inlet portion, the one or more cold plates being supported in thermal contact with at least a portion of the air inflow channel.

8. The air sampling system of claim 7, wherein the one or more cold plates are made of aluminum.

9. The air sampling system of claim 1, further comprising an air pump for drawing air out of the collection chamber via an air outflow channel.

10. The air sampling system of claim 1, further comprising a temperature sensor for measuring a temperature of the air in the air inflow channel and wherein the controller is configured to control the cooling unit based on measurements obtained from the temperature sensor.

11. The air sampling system of claim 1, wherein the collection chamber includes an active target substrate having a surface that is coated with bioreceptors and wherein the air sampling system further comprises an optical detection unit that is configured to illuminate the active target substrate with a light source.

12. The air sampling system of claim 11, wherein the bioreceptors comprise antibodies.

13. The air sampling system of claim 1, further comprising:
- a liquid inflow channel having a liquid inflow port, the liquid inflow channel being fluidly connected to the collection chamber;
- a liquid outflow channel that is fluidly connected to the collection chamber; and
- a liquid pump for causing liquid to flow into and out of the collection chamber.

14. The air sampling system of claim 13, further comprising a flow sensor associated with at least one of the liquid inflow channel or the liquid outflow channel for measuring a rate of flow of liquid out of the collection chamber and wherein the controller is configured to control the cooling unit based on measurements obtained from the flow sensor.

15. The air sampling system of claim 1, further comprising a hygroscopic filter that removes liquid from air that is expelled out of the collection chamber.

16. The air sampling system of claim 1, wherein the collection chamber is removably coupled to the air inflow channel.

17. The air sampling system of claim 1, further comprising a plurality of glass beads disposed inside the collection chamber, the surfaces of the plurality of glass beads being exposed to liquid collected in the collection chamber.

18. The air sampling system of claim 1, further comprising a notification unit for generating signals representing notifications indicating detection of one or more target analytes in the liquid collected in the collection chamber.

* * * * *